(12) United States Patent
Yamaguchi

(10) Patent No.: US 10,463,705 B2
(45) Date of Patent: Nov. 5, 2019

(54) METHOD FOR TREATING DISEASE ASSOCIATED WITH TRANSCRIPTION ACTIVATION BY NF-κB

(71) Applicant: MARUHACHI MURAMATSU, INC., Shizuoka (JP)

(72) Inventor: Masayoshi Yamaguchi, Shizuoka (JP)

(73) Assignee: Maruhachi Muramatsu, Inc., Shizuoka (JP)

( * ) Notice: Subject to any disclaimer, the term of this patent is extended or adjusted under 35 U.S.C. 154(b) by 504 days.

(21) Appl. No.: 15/200,234

(22) Filed: Jul. 1, 2016

(65) Prior Publication Data

US 2016/0310550 A1 Oct. 27, 2016

Related U.S. Application Data

(63) Continuation of application No. 14/478,192, filed on Sep. 5, 2014, now abandoned, which is a continuation of application No. 13/849,005, filed on Mar. 22, 2013, now abandoned.

(30) Foreign Application Priority Data

Apr. 2, 2012 (JP) ................................. 2012-083919

(51) Int. Cl.
*A61K 36/03* (2006.01)

(52) U.S. Cl.
CPC ..................................... *A61K 36/03* (2013.01)

(58) Field of Classification Search
CPC ............................... A61K 36/02; A61K 36/03
USPC .................................................... 424/195.17
See application file for complete search history.

(56) References Cited

U.S. PATENT DOCUMENTS

| 2003/0068330 A1* | 4/2003 | Goto | A61K 31/122 |
| | | | 424/195.17 |
| 2009/0170810 A1* | 7/2009 | Hao | A61K 9/0019 |
| | | | 514/54 |
| 2010/0021494 A1* | 1/2010 | Yuasa | A61K 36/03 |
| | | | 424/195.17 |
| 2010/0247564 A1* | 9/2010 | Lee | A61K 36/03 |
| | | | 424/195.17 |

FOREIGN PATENT DOCUMENTS

| JP | 2004-217559 A | 8/2004 |
| JP | 3749978 B2 | 12/2005 |
| JP | 2006-022033 A * | 1/2006 |
| JP | 2008-120702 A * | 5/2008 |
| JP | 2008-214245 A * | 9/2008 |
| JP | 2009-242325 A * | 10/2009 |
| JP | 2011-168573 A | 9/2011 |

OTHER PUBLICATIONS

Alles et al., "Suppression of NF-κB Increases Bone Formation and Ameliorates Osteopenia in Ovariectomized Mice," Endocrinology, Oct. 2010, 151(10:4626-4634.

Matsumoto et al., "Effect of *Sargassum horneri* Extract on Circulating Bone Metabolic Markers: Supplemental Intake Has an Effect in Healthy Humans," Journal of Health Science, 2008, 54(1):50-55.

Uchiyama et al., "Stimulatory Effect of *Sargassum horneri* Extract on Bone Formation in Rat Femoral-Diaphyseal and -Metaphyseal Tissues in Vitro," Journal of Health Science, 2002, 48(2):148-153.

Uchiyama et al., "Inhibitory Effect of Marine Alga *Sargassum horneri* Extract on Bone Resorption in Tissue Culture in Vitro," Journal of Health Science, 2002, 48(2):154-160.

Uchiyama et al., "Anabolic Effect of Marine Alga *Sargassum horneri* Extract on Bone Components in the Femoral-diaphyseal and -metaphyseal Tissues of Young and Aged Rats in Vitro," Journal of Health Science, 2002, 48(4):325-330.

Uchiyama et al., "Preventive Effect of Marine Alga *Sargassum horneri* Extract on Bone Loss in Streptozotocin-Diabetic Rats in Vitro," Journal of Health Science, 2003, 49(2):149-155.

Uchiyama et al., "Characterization of Active Component in Marine Alga *Sargassum horneri* Extract in Stimulating Bone Calcification in Vitro," Journal of Health Science, 2004, 50(6):634-639.

Yamaguchi et al., "Effect of Marine Algae Extract on Bone Calcification in the Femoral-metaphyseal Tissues of Rats: Anabolic Effect of *Sargassum horneri*," Journal of Health Science, 2001, 47(6):533-538.

Yamaguchi et al., "Bone Metabolism Regulation Function of Marine Algae *Sargassum horneri* Component: Development of Novel Functional Material Hormax® Which Prevents Osteoporosis," New Food Industry, 2008, 50(1):1-6, with concise explanation in English.

Yamaguchi et al., "Vitamin K2 stimulates osteoblastogenesis and suppresses osteoclastogenesis by suppressing NF-κB activation," International Journal of Molecular Medicine, 2011, 27:3-14.

Yamaguchi et al., "Marine algae *Sargassum horneri* bioactive factor stimulates osteoblastogenesis and suppresses osteoclastogenesis in vitro," OA Biotechnology, Nov. 2012, 1(1):1-7.

Hoshino et al., "An Antivirally Active Sulfated Polysaccharide from *Sargassum homeri* (Turner) C. Agardh," Biol. Pharm Bull., 1998, 21(7):730-734.

Kim et al., "Fucoxanthin inhibits the inflammatory response by suppressing the activation of NF-κB and MAPKs in lipopolysaccharide-induced RAW 264.7 macrophages," European Journal of Pharmacology, 2010, 649(1-3):369-375.

Matsuda et al., "Anticancer Benefit of *Sargassum horneri* Extract," Bulletin of Fisheries Sciences, Hokkaido University, 2005, 56(3):75-86, with English abstract on first page.

Matsumoto et al., "Marine algae *Sargassurn horneri* extract component exerting effect of increasing bone mass: regarding bone formation promoting-factor," Meeting of Japan Society of Nutrition and Food Science, Summaries of lectures, Apr. 20, 2007, p. 232, 41-1p.

(Continued)

*Primary Examiner* — Aaron J Kosar

(74) *Attorney, Agent, or Firm* — Foley & Lardner LLP

(57) ABSTRACT

A method for treating a disease associated with transcription activation by NF-κB by administering a composition for inhibiting transcription activation by NF-κB to a patient in need of treatment of the disease. The composition contains a fraction having a molecular weight of 3,000 or less obtained by purifying a water extract of *Sargassum horneri* as an active ingredient.

1 Claim, 2 Drawing Sheets

(56) References Cited

OTHER PUBLICATIONS

Yamamoto et al., "Fucoxanthin and its deacetylated product, fucoxanthinol, induce apoptosis of primary effusion lymphomas," Cancer Letters, 2011, 300(2):225-234.

* cited by examiner

[Figure 1]
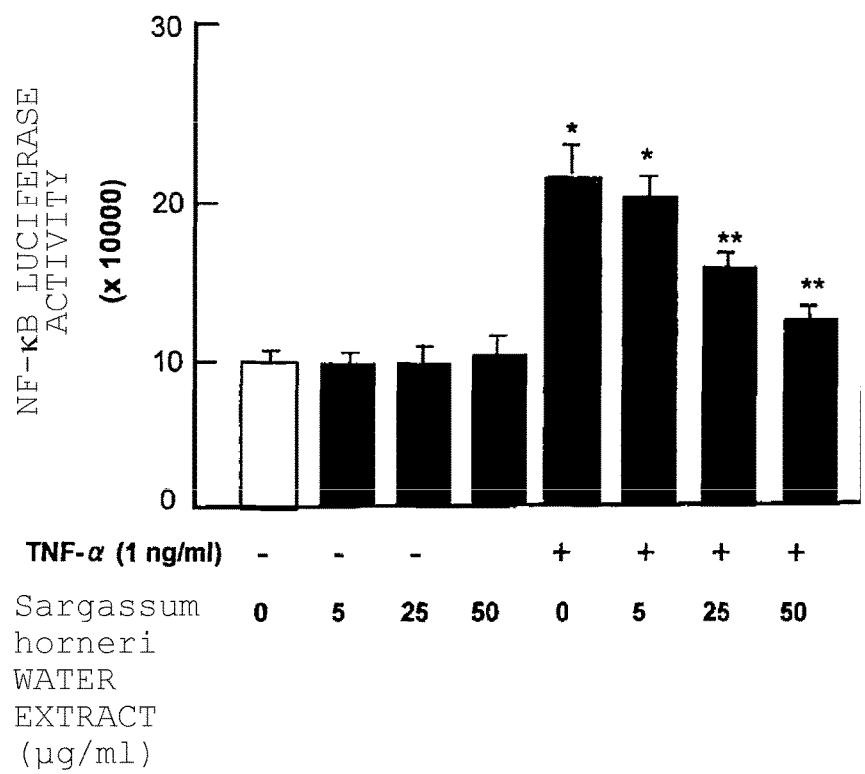

[Figure 2]
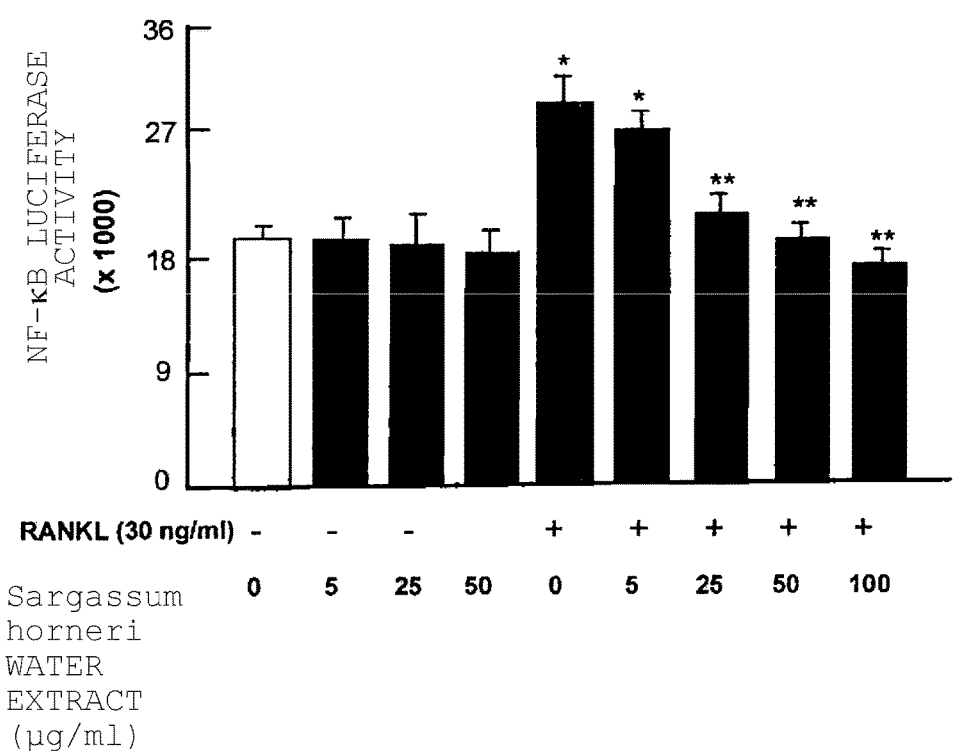

METHOD FOR TREATING DISEASE ASSOCIATED WITH TRANSCRIPTION ACTIVATION BY NF-κB

CROSS-REFERENCE TO RELATED APPLICATIONS

This application is a Continuation of U.S. patent application Ser. No. 14/478,192, filed Sep. 5, 2014, which is a Continuation of U.S. patent application Ser. No. 13/849,005, filed Mar. 22, 2013, which claims priority from Japanese application JP 2012-083919, filed Apr. 2, 2012.

TECHNICAL FIELD

The present invention relates to an NF-κB inhibitor comprising *Sargassum horneri* or a processed product of *Sargassum horneri* such as a *Sargassum horneri* water extract having a molecular weight of 3,000 or less, and a composition for inhibiting transcription activation by NF-κB, comprising such an NF-κB inhibitor.

BACKGROUND ART

NF-κB (nuclear factor κB) is a protein complex which serves as a transcription factor, and known to activate transcription of a variety of genes which control inflammation, immune reaction, cell proliferation, apoptosis and the like and HIV-1 (human immunodeficiency virus type 1), which is a causative virus of AIDS (acquired immunodeficiency syndrome). In addition, NF-κB is known to be constantly activated in inflammatory diseases such as Crohn's disease, bronchial asthma, inflammatory bowel disease, arthritis and sepsis and many malignant tumors. Therefore, it is thought that an inhibitor against NF-κB is effective in a treatment for these diseases.

NF-κB is usually associated with IκB (Inhibitor κB), a protein (inhibitor) which suppresses NF-κB activation, in the cytoplasm. It is known that: when a cell is stimulated by an inflammatory cytokine such as TNF-α (tumor necrosis factor-α) or IL-1 (interleukin-1), an IKK (IκB kinase) complex is activated by a kinase such as MEKK 1, 3 (mitogen-activated protein kinase/extracellular signal-regulated kinase kinase 1, 3) and NIK (NF-κB inducing kinase); the activated IKK complex phosphorylates two specific serine residues in IκB, and the phosphorylated IκB is polyubiquitinated and degraded by 26S proteasome; a nuclear localization signal (NLS) in NF-κB is then exposed; and NF-κB from which IκB is dissociated translocates into the nucleus and activates transcription of target genes.

In recent years, studies and development which position an NF-κB inhibitor as a candidate for a new antiinflammatory agent, antineoplastic drug and the like are vigorously carried out, and some NF-κB inhibitors consisting of a low molecular weight compound have been reported; such low molecular weight compounds have a variety of mechanisms of action. For example, PS-341 (Bortezomib), which is in a clinical trial for a therapeutic agent for myeloma, is a 26S proteasome inhibitor, and has been reported to show an inhibitory effect on NF-κB by suppressing degradation of IκB. It has been reported that DHMEQ (Dehydroxymethyl epoxyquinomycin) suppresses transcription activation by NF-κB by inhibiting nuclear import of NF-κB and induces apoptosis of a variety of myeloma cells. In addition, among gold compounds which are antirheumatic drugs, AuTG (aurothioglucose), in particular, has been reported to inhibit DNA binding of NF-κB through redox control. In addition, it has been reported that vitamin K2 suppresses activation of NF-κB by increasing the expression of IκB mRNA in osteoblasts and osteoclast precursor cells (Non-patent Document 1). Furthermore, it has been reported that S1627 suppresses transcription activation by NF-κB by inhibiting DNA binding of NF-κB, to increase bone formation and also improve osteopenia (Non-patent Document 2).

Up to now, the present inventors have carried out a basic study related to prevention and repair of osteoporosis by food factors. In the course of the study, they have reported ahead of the nation and foreign countries that, among edible marine algae, marine algae *Sargassum horneri* extract has an effect of promoting bone formation (Patent Document 1, Non-patent Documents 3 to 10). However, it was not clear whether the marine algae *Sargassum horneri* extract has an NF-κB inhibitory effect.

PRIOR ART DOCUMENTS

Patent Document

[Patent Document 1] Japanese Patent No. 3749978

Non-Patent Documents

[Non-patent Document 1] Yamaguchi M. and Weitzmann M. N.: Int J Mol Med 27: 3-14 (2011).
[Non-patent Document 2] Alles N. et al.: Endocrinology 151: 4626-4634 (2010).
[Non-patent Document 3] Yamaguchi M. et al.: J. Health Sci. 47: 533-538 (2001).
[Non-patent Document 4] Uchiyama S. and Yamaguchi M.: J. Health Sci. 48: 148-153 (2002).
[Non-patent Document 5] Uchiyama S. and Yamaguchi M.: J. Health Sci. 48: 154-160 (2002).
[Non-patent Document 6] Uchiyama S. et al.: J. Health Sci. 50: 634-639 (2004).
[Non-patent Document 7] Uchiyama S. and Yamaguchi M.: J. Health Sci. 48: 325-330 (2002).
[Non-patent Document 8] Uchiyama S. and Yamaguchi M.: J. Health Sci. 49: 149-155 (2003).
[Non-patent Document 9] Matsumoto T. et al.: J. Health Sci. 54: 50-55 (2008).
[Non-patent Document 10] Masayoshi Yamaguchi, Toru Matsumoto, Yoshinori Hokari and Masayuki Hashizume: Kaisou Akamoku Seibun no Kotsutaisha Chousetsu Kinou: Kotsusoshoushou wo Yobou Suru Sinki Kinousei Sozai Hormax (R) no Kaihatsu (Bone Metabolism Regulation Function of Marine Algae *Sargassum horneri* Component: Development of Novel Functional Material Hormax (R) Which Prevents Osteoporosis). New Food Industry, 50(1), 1-6 (2008).

SUMMARY OF THE INVENTION

Object to be Solved by the Invention

An object of the present invention is to provide an NF-κB inhibitor which can be easily obtained and consumed in daily dietary life and which can inhibit transcription activation by NF-κB.

Means to Solve the Object

The present inventors have vigorously carried out a study about factors involved in the effect of promoting bone formation by marine algae *Sargassum horneri* extracts. As candidates for such factors, as described in the document (Boyle W. et al.: Nature. 423: 337-342 (2003)), the document (Zaidi M.: Nature Medicine: 791-801 (2007)) and the like, a number of factors such as a factor involved in differentiation of osteoclasts, a factor which proliferates osteoclasts, a factor involved in bone resorption of osteoclasts and a factor which promotes osteoblastogenesis are known. While analysis proceeded following the present inventors' experience for long years and hunches, the present inventors found that a *Sargassum horneri* water extract having a molecular weight of 3,000 or less inhibits transcription activation by NF-κB in an osteoblast in which NF-κB is activated by TNF-α. Furthermore, it was confirmed that a *Sargassum horneri* water extract having a molecular weight of 3,000 or less also inhibits transcription activation by NF-κB in osteoclast precursor cells in which NF-κB is activated by RANKL (receptor activator of NF-κB (RANK) ligand). The present invention has reached completion on the basis of these findings.

Therefore, the present invention relates to: (1) an NF-κB inhibitor comprising *Sargassum horneri* or a processed product thereof as an active ingredient; (2) the NF-κB inhibitor according to the above-mentioned (1), wherein the processed product of *Sargassum horneri* is an extract of *Sargassum horneri*; (3) the NF-κB inhibitor according to the above-mentioned (2), wherein the extract of *Sargassum horneri* is a water extract of *Sargassum horneri*; and (4) the NF-κB inhibitor according to the above-mentioned (3), wherein the water extract of *Sargassum horneri* is a *Sargassum horneri* water extract having a molecular weight of 3,000 or less.

In addition, the present invention relates to (5) a composition for inhibiting transcription activation by NF-κB, comprising the NF-κB inhibitor according to any one of the above-mentioned (1) to (4).

Effect of the Invention

By means of the present invention, an NF-κB inhibitor which can be easily obtained and consumed in daily dietary life, whose active ingredient is marine algae *Sargassum horneri* or a processed product thereof, especially a water extract having a molecular weight of 3,000 or less can be provided. In addition, when the NF-κB inhibitor of the present invention is used, an inflammatory disease or a malignant tumor in which NF-κB is constantly activated can be treated.

BRIEF DESCRIPTION OF DRAWINGS

FIG. 1 shows that transcription activation by NF-κB is inhibited by the *Sargassum horneri* water extract of the present invention, using osteoblasts in which NF-κB is activated by TNF-α. In the figure, "*" indicates that, as compared with the group which did not receive any of TNF-α and the *Sargassum horneri* water extract (the first bar from the left), there is a statistically significant difference (P<0.001). In addition, in the figure, indicates that, as compared with the group which received TNF-α (the fifth bar from the left), there is a statistically significant difference (P<0.001).

FIG. 2 shows that transcription activation by NF-κB is inhibited by the *Sargassum horneri* water extract of the present invention, using osteoclast precursor cells in which NF-κB is activated by RANKL. In the figure, "*" indicates that, as compared with the group which did not receive any of RANKL and the *Sargassum horneri* water extract (the first bar from the left), there is a statistically significant difference (P<0.001). In addition, in the figure, "**" indicates that, as compared with the group which received RANKL (the fifth bar from the left), there is a statistically significant difference (P<0.001).

MODE OF CARRYING OUT THE INVENTION

The NF-κB inhibitor of the present invention has an action of inhibiting transcription activation by NF-κB. The inhibitory action of transcription activation by NF-κB includes, for example, an action of inhibiting phosphorylation of IκB, which is an inhibitor of NF-κB, and thereby inhibiting degradation of IκB and inhibiting activation of NF-κB, an action of inhibiting activation of NF-κB by increasing expression of IκB, an action of suppressing and inhibiting mRNA expression of a gene which is a target of NF-κB, by inhibiting nuclear import of NF-κB from which IκB is dissociated, and an action of suppressing or inhibiting mRNA expression of a target gene of NF-κB by inhibiting binding of NF-κB imported into the nucleus to a regulatory region (DNA) of the target gene.

The NF-κB inhibitor of the present invention is not limited specifically, so long as the inhibitor comprises *Sargassum horneri* or a processed product thereof as an active ingredient, and such *Sargassum horneri* or a processed product thereof includes a dried product of *Sargassum horneri* obtained by drying the whole of *Sargassum horneri*, a dry powder of *Sargassum horneri* obtained by subjecting dried *Sargassum horneri* to a powderization treatment, a *Sargassum horneri* water extract obtained by separating soluble components using water such as room-temperature water, hot water and deionized water, a *Sargassum horneri* organic solvent extract obtained by separating soluble components using an organic solvent such as alcohol water and hexane, and a *Sargassum horneri* enzyme-treated product obtained by treating *Sargassum horneri* using an enzyme such as cellulase. Among the above, a *Sargassum horneri* organic solvent extract and a *Sargassum horneri* water extract are preferable products, which may be preferably exemplified by a water extract of *Sargassum horneri*.

While the above-mentioned *Sargassum horneri* organic solvent extract and *Sargassum horneri* water extract can be directly used as an active ingredient of the NF-κB inhibitor, it is also possible to use a fraction with higher NF-κB inhibitory activity fractionated from the extract by an appropriate purification means, for example, silica gel column chromatography, reverse-phase column chromatography, gel filtration chromatography and membrane filtration. The fraction with higher NF-κB activity may be preferably exemplified by a fraction having a molecular weight of 50,000 or less, preferably a molecular weight of 10,000 or less, more preferably a molecular weight of 5,000 or less, still more preferably a molecular weight of 3,000 or less.

Methods for preparing the *Sargassum horneri* dried product include a method of washing fresh *Sargassum horneri* with water, and thereafter drying it by lyophilization, solar drying, air drying, hot-air drying, heated-air drying, microwave drying or the like, and methods for preparing the *Sargassum horneri* dry powder include a method of drying fresh *Sargassum horneri*, and thereafter powdering it with a mixer or the like. Methods for preparing the *Sargassum horneri* organic solvent extract and the *Sargassum horneri* water extract specifically include a method of obtaining an extract by adding to crushed fresh *Sargassum horneri* with a homogenizer or the like, 1 to 5 times, preferably 2 to 4 times, and especially preferably about 3 times the amount of water such as room-temperature water, hot water or deionized water, or 5 to 80%, preferably 10 to 40%, and more preferably about 20% alcohol in water such as methanol, ethanol or propanol in water, or an organic solvent such as hexane to carry out an extraction, and separating a soluble fraction by centrifugation at 4,000 to 7,000 g and preferably 5,000 to 6,000 g for 5 to 15 minutes and preferably about 10 minutes, which may be preferably exemplified by a method of adding to the crushed *Sargassum horneri* about 3 times the amount of water to carry out an extraction and separating a soluble fraction by centrifugation at 5,000 to 6,000 g for about 10 minutes. In addition, intact *Sargassum horneri*, which is not crushed, may be used to carry out the extraction from *Sargassum horneri*, in which case the *Sargassum horneri* is preferably crushed with a homogenizer or the like after the extraction. When harvested *Sargassum horneri* is not immediately processed, the *Sargassum horneri* is preferably stored at a low temperature of 10° C. or below, for example, at 4 to 5° C.

It can be confirmed that the prepared processed product of *Sargassum horneri* has inhibitory action on transcription activation by NF-κB by analyzing mRNA expression of a gene which is a target of NF-κB or expression of a protein translated from mRNA of a gene which is a target of NF-κB, using the known molecular biological technique. Methods for analyzing mRNA expression of a gene which is a target of NF-κB specifically include, for example, quantitative RT-PCR (Reverse Transcription Polymerase Chain Reaction), RT-PCR and Southern blotting, and methods for analyzing expression of a protein translated from mRNA of a gene which is a target of NF-κB specifically include, for example, Western blotting, reporter assay using a plasmid to which a reporter gene such as luciferase is inserted downstream of a promoter regulated by NF-κB and mass spectrometry.

The composition for inhibiting transcription activation by NF-κB of the present invention is not limited specifically so long as the composition comprises the NF-κB inhibitor of the present invention, and may be exemplified by a composition in which a formulation component such as a pharmaceutically acceptable usual carrier, binding agent, stabilizing agent, excipient, diluent, pH buffer, disintegrant, solubilizer, solubilizing agent or isotonic agent is added to the NF-κB inhibitor in a case where the NF-κB inhibitor of the present invention is used as a therapeutic agent for medicinal purpose, and a composition in which a component such as an antiseptic, antioxidant, colorant or sweetening is added in a case where the NF-κB inhibitor of the present invention is used as a supplement.

A dosage form of the NF-κB inhibitor or the composition for inhibiting transcription activation by NF-κB of the present invention includes oral administration in which administration is carried out in a formulation such as a powder, granule, tablet, capsule, syrup or suspension, and parenteral administration in which a formulation such as a solution, emulsion or suspension is injected or intranasally administered in a form of a spray. In addition, the NF-κB inhibitor and the composition for inhibiting transcription activation by NF-κB of the present invention can be used as a medicine, supplement or functional food for treatment or prevention of a disease associated with activation of NF-κB. Examples of the disease associated with activation of NF-κB include: cancer such as colon cancer, rectal cancer, prostate cancer, cervical cancer, hematological cancer, larynx cancer, liver cancer, lung cancer, pharyngeal cancer, testicular cancer, bladder cancer, ovarian cancer, uterus cancer, bronchus cancer, pancreatic cancer, neck cancer, stomach cancer, skin cancer, kidney cancer, esophagus cancer and mouth cancer; inflammation such as asthma, bronchitis, allergic rhinitis, chronic obstructive pulmonary disease, Lou Gehrig's disease, septicemia, conjunctivitis, purpura, nasal polyp, lupus erythematosus, acute respiratory distress syndrome, Crohn's disease, gastritis, esophagitis, hepatitis, pancreatitis, nephritis, irritable bowel syndrome, mucous colitis, ulcerative colitis, osteoarthritis, gout, psoriasis, eczema, dermatitis, chronic rheumatoid arthritis, rheumatoid spondylitis, cystic fibrosis, inflammatory bowel disease and multiple sclerosis; and autoimmune diseases and infectious diseases such as systemic scleroderma, Behcet disease, periarteritis nodosa, ulcerative colitis, chronic rheumatoid arthritis, systemic lupus erythematosus, active chronic hepatitis, glomerulonephritis, acquired immune deficiency syndrome (AIDS), an infectious disease by human papillomavirus, an infectious disease by human T cell leukemia virus, an infectious disease by hepatitis B virus and an infectious disease by hepatitis C virus.

In addition, examples of the above-mentioned functional food include: a variety of drinks such as yogurt, yogurt drink, juice, milk, soymilk, alcoholic drinks, coffee, black tea, green tea, oolong tea and sports drink; bread and confectionary such as pudding, cookie, bread, cake, jelly, baked goods such as rice cracker, Japanese confectionary such as yokan (azuki-bean jelly), frozen dessert and chewing gum; noodles such as udon and soba; fish-paste products such as steamed fish paste, ham and fish sausage; seasonings such as miso, soy sauce, dressing, mayonnaise and sweetener; dairy products such as cheese and butter; tofu; konjac; and other variety of household dishes such as preservable food boiled down in soy, jiaozi, croquette and salad.

The present invention will be explained below more in detail by Examples, but the technical scope of the present invention is not limited to these exemplifications.

EXAMPLES

Example 1

1. Materials

As *Sargassum horneri*, *Sargassum horneri* harvested from the coast at Iwate prefecture was used. The *Sargassum horneri* was ground, and thereafter purified distilled water was added to the obtained *Sargassum horneri* ground product. The mixture was subjected to suspension extraction with a Potter homogenizer for 10 to minutes, and the extract was centrifuged using a centrifuge at room temperature (10 to 25° C.) at 3,000 rotations for 30 minutes. After the centrifugation, a supernatant thereof was recovered, and a *Sargassum horneri* water extract having a molecular weight of 3,000 or less was isolated by membrane filtration. Such a *Sargassum horneri* water extract was freeze-dried, and dissolved in purified distilled water to be used, when used in an experiment.

Example 2

2. Method 2-1 Method of Pre-Incubation of Osteoblast

Osteoblasts were pre-incubated in accordance with the method described in the document (Yamaguchi M, Weitzmann M N: Vitamin $K_2$ stimulates osteoblastogenesis and suppresses osteoclastogenesis by NF-κB activation. Int J Mol Med 27: 3-14 (2011)). That is to say, 1 ml of α-MEM (α-modified essential medium) (manufactured by Invitrogen Corporation) culture solution containing 10% fetal bovine serum (FBS) (hereinafter simply referred to as culture solution) was added to a 12-well culture plate, osteoblasts (the number of cells: $1 \times 10^5$ cells/ml/well) were transferred into the culture solution, and pre-incubation was carried out at 37° C. in a $CO_2$ incubator for 3 days.

2-2 Method of Calcification (Mineralization) Analysis of Osteoblast Using *Sargassum horneri* Water Extract Calcification analysis of osteoblasts using the *Sargassum horneri* water extract was carried out in accordance with the procedure shown in the following [1] to [8], on the basis of the method described in the document (Yamaguchi M, Weitzmann M N: Vitamin $K_2$ stimulates osteoblastogenesis and suppresses osteoclastogenesis by NF-κB activation. Int J Mol Med 27: 3-14 (2011)).

[1] The osteoblasts pre-incubated by the method described in the item "2-1 Method of Pre-incubation of Osteoblast" was cultured in a culture solution (0.8 ml) containing a calcification substrate (100 μg/ml L-ascorbic acid and 4 mM β-glycerophosphate), TNF-α (5 ng/ml) (manufactured by Sigma-Aldrich Corporation) and the *Sargassum horneri* water extract isolated by the method described in Example 1 (5, 10 and 25 μg/ml culture solution) for 21 days. Here, as a control, a culture solution, a culture solution containing a calcification substrate and a culture solution containing a calcification substrate and TNF-α were used. Each culture solution was changed to fresh culture solution every 3 days.

[2] One milliliter of saline (phosphate buffered saline; PBS) was added to each of the culture plate, from which the culture solution was removed, and the cells were washed.

[3] Thereafter, 75% ethanol cooled down at 4° C. (0.5 ml) was added to each culture plate, and left standing still at 4° C. for 30 minutes, thereby the cells were fixed, and then the ethanol was removed.

[4] One milliliter of purified distilled water was added to wash the cells, and then the cells were subjected to air dried for 2 hours.

[5] After the air drying, 0.5 ml of 40 mM 1% alizarin red (Alizarin Red-S) was added to each culture plate, and the culture plate was left standing still at room temperature for 30 minutes, and alizarin red staining was carried out.

[6] The stain solution was removed, and 1 ml of purified distilled water was added thereto. Washing was repeated 4 times.

[7] After the washing, the plates were air dried overnight, and the stained culture plate was photographed with a scanner, and stored as data.

[8] For quantification of calcification of the osteoblasts, 10% cetylpyridinium chloride solution (manufactured by Sigma-Aldrich Corporation) was added to the dried culture plate to dissolve calcified calcium, and absorption was determined at a wavelength of 570 nm using a microplate reader.

2-3 Method of Luciferase Assay 2-3-1 Method of Luciferase Assay Using Osteoblast A method of luciferase assay using osteoblasts was carried out in accordance with the procedure shown in the following [1] to [5], on the basis of the method described in the document (Yamaguchi M, Weitzmann M N: Vitamin $K_2$ stimulates osteoblastogenesis and suppresses osteoclastogenesis by NF-κB activation. Int J Mol Med 27: 3-14 (2011)).

[1] Osteoblasts ($2 \times 10^4$ cells/0.1 ml/well) were cultured for 24 hours, and 1 ng/ml nuclear factor-kappa B (NF-κB)-luciferase plasmid (NF-κB-luciferase plasmid) (manufactured by Bioscience) in culture solution was transfected into the cultured osteoblast.

[2] After the transfection and culture for 5 hours, the medium was changed to a *Sargassum horneri* water extract-containing culture solution that contains TNF-α (1 ng/ml culture solution) (manufactured by Santa Cruz Biotechnology, Inc.) and a *Sargassum horneri* water extract isolated by the method described in Example 1 (5, 25, 50 or 100 μg/ml culture solution), and the cells were cultured for 24 hours. Here, as a control, cells cultured in a culture solution, a culture solution containing TNF-α and a culture solution containing a *Sargassum horneri* water extract (5, 25, 50 or 100 μg/ml culture solution) were used.

[3] After the culture, the *Sargassum horneri* water extract-containing culture solution was removed, and a cell lysis solution (manufactured by Promega KK, 20 μl) was added to the culture plate, and the cells were lysed with shaking for 30 minutes.

[4] A substrate solution of luciferase assay was added to the obtained cell lysate, and luminescence intensity was counted with a luminoassay (manufactured by Turner Designs).

[5] Luciferase activity was indicated as the number of determination count (arbitrary unit).

2-3-2 Method of Luciferase Assay Using Osteoclast

A method of luciferase assay using osteoclasts was carried out in accordance with the procedure shown in the following [1] to [5], on the basis of the description of the document (Yamaguchi M, Weitzmann M N: Vitamin $K_2$ stimulates osteoblastogenesis and suppresses osteoclastogenesis by NF-κB activation. Int J Mol Med 27: 3-14 (2011)).

[1] Osteoclast precursor cells (RAW267.4) ($2 \times 10^4$ cells/0.1 ml/well) were cultured for 24 hours, and NF-κB-luciferase plasmid (manufactured by Bioscience) was transfected into the cultured osteoclast precursor cells.

[2] After the transfection and culture for 5 hours, the medium was changed to a *Sargassum horneri* water extract-containing culture solution that contains RANKL (30 ng/ml culture solution) (manufactured by R & D Systems, Inc.) and the *Sargassum horneri* water extract isolated by the method described in Example 1 (5, 25, 50 or 100 μg/ml culture solution), and the cells were cultured for 24 hours. Here, as a control, cells cultured in a culture solution, a culture solution containing TNF-α and a culture solution containing a *Sargassum horneri* water extract (5, 25, 50 or 100 μg/ml culture solution) were used.

[3] After the culture, the *Sargassum horneri* water extract-containing culture solution was removed, and a cell lysis solution (manufactured by Promega KK, 20 μl) was added to the culture plate, and the cells were lysed with shaking for 30 minutes.

[4] A substrate solution of luciferase assay was added to the obtained cell lysate, and luminescence intensity was counted with a luminoassay (manufactured by Turner Designs).

[5] Luciferase activity was indicated as the number of determination count (arbitrary unit).

2-4 Method of Analysis of Osteoclastogenesis

In a *Sargassum horneri* water extract-containing culture solution that contains RANKL (30 ng/ml culture solution) (manufacture by R & D Systems, Inc.) cross-linked with anti-poly-histidine antibody (2.5 μg/ml) (manufactured by R & D Systems, Inc.), which induces osteoclastogenesis, and the *Sargassum horneri* water extract isolated by the method described in Example 1 (5, 25, 50 or 100 μg/ml culture solution), osteoclast precursor cells (RAW267.4) ($1 \times 10^4$ cells/0.2 ml culture solution/well) were cultured for 6 days. Here, as a control, cells cultured in a culture solution were used. After the culture, the formed osteoclasts were stained using leukocyte acid phosphatase kit (manufactured by Sigma-Aldrich Corporation) utilizing tartrate resistant acid phosphatase (TRAP) activity, which enzyme is a marker enzyme of osteoclasts. Osteoclasts having 3 or more nuclei were counted as TRAP-positive cells.

2-5 Statistical Processing

Significant difference of each value was analyzed using one-way analysis of variance (ANOVA) and Tukey-Kramer multiple comparisons post test. When p was <0.05, it was regarded that there was a significant difference.

Example 3

3. Results and Discussion 3-1 NF-κB Activation Inhibitory Effect of *Sargassum horneri* Water Extract of the Present Invention in Osteoblast TNF-α regulates diverse cellular functions via NF-κB activation signal in the cell, and, for example, in osteoblasts, it is known that TNF-α suppresses calcification of osteoblasts (Non-patent Documents 4, 5, Yamaguchi M, Weitzmann M N: Vitamin $K_2$ stimulates osteoblastogenesis and suppresses osteoclastogenesis by NF-κB activation. Int J Mol Med 27: 3-14 (2011), Li Y, Li A, Strait K, Zhang H, Nanes M S and Weitzmann M N: Endogenous TNF alpha Lowers Maximum Peak Bone Mass and Inhibits Osteoblastic Smad Activation, through NF-kappa B. J Bone Miner Res 22: 646-655 (2007)). Also in the present experiment, it was confirmed that, when osteoblasts were cultured after TNF-α (1 ng/ml culture solution) was added, calcification of the osteoblasts was inhibited. It was revealed that such calcification inhibition by TNF-α in osteoblasts is significantly suppressed by addition of the *Sargassum horneri* water extract isolated by the method described in Example 1 (50 and 100 μg/ml culture solution).

Although a number of factors involved in calcification inhibition via TNF-α in osteoblasts are known, analysis was proceeded focusing on NF-κB, among the factors. First, in osteoblasts, it was confirmed that NF-κB-dependent transcription activation by TNF-α is induced (FIG. 1, the fifth bar from the left). It was revealed that such transcription activation by NF-κB is significantly suppressed (p<0.001) by addition of the *Sargassum horneri* water extract (25, 50 and 100 μg/ml) (FIG. 2, the 7th to 9th bars from the left).

The above-mentioned results show that the *Sargassum horneri* water extract of the present invention inhibits activation of NF-κB in osteoblasts, and also suggest that the *Sargassum horneri* water extract of the present invention has an action of suppressing function deterioration of an osteoblast caused by TNF-α increase in serum in a disease state and promoting bone repair by calcification of the osteoblasts.

3-2 Effect of *Sargassum horneri* Water Extract of the Present Invention on NF-κB Activation of Osteoclast Precursor Cell Increased by RANKL It is known that, in osteoclast precursor cells, when induction of differentiation into osteoclasts via RANK, which is a receptor of RANKL, occurs, osteoclasts are formed. An inhibitory effect of the *Sargassum horneri* water extract (5, 25, 50 and 100 μg/ml) in such osteoclastogenesis was examined. As a result, it was revealed that osteoclastogenesis by RANKL (30 ng/ml) is significantly suppressed (P<0.01) by addition of the *Sargassum horneri* water extract (50 and 100 μg/ml). Note that it was confirmed that the inhibitory effect of osteoclastogenesis by the *Sargassum horneri* water extract is not obtained due to cytotoxicity.

Although a number of factors involved in osteoclastogenesis via RANKL in osteoclast precursor cells are known, analysis was proceeded focusing on NF-κB, among the factors. First, in osteoclast precursor cells, it was confirmed that RANKL-dependent transcription activation by NF-κB is induced (FIG. 2, the fifth bar from the left). It was revealed that such transcription activation by NF-κB is significantly suppressed (p<0.001) by addition of the *Sargassum horneri* water extract (25, 50 and 100 μg/ml) (FIG. 2, the 7th to 9th bars from the left).

The above-mentioned results show that the *Sargassum horneri* water extract of the present invention inhibits activation of NF-κB in osteoclast precursor cells, and also suggest a possibility that the *Sargassum horneri* water extract of the present invention can suppress articular bone destruction by promotion of osteoclastogenesis from osteoclast precursor cells by RANKL, which increases at the time of arthritis.

INDUSTRIAL APPLICABILITY

The present invention can treat an inflammatory disease or a malignant tumor in which NF-κB is constantly activated, by using marine algae *Sargassum horneri* or a processed product thereof, especially a water extract having a molecular weight of 3,000 or less, as an active ingredient. In addition, since the present invention is a preparation derived from *Sargassum horneri*, which is marine algae whose history as a food is long, the present invention is highly secure, and can be routinely consumed for the purpose of prevention since one's youth. Therefore, it can be expected that the present invention not only contributes to healthy life of an individual's old age, but also contributes to reduction of medical costs in aging society.

The invention claimed is:

1. A method for treating an inflammation disorder associated with NF-kB-mediated transcriptional activation in a patient in need thereof, the method comprising administering a composition for inhibiting NF-kB-mediated transcriptional activation to the patient, wherein the composition has an isolated fraction having a molecular weight of 3,000 or less obtained by purifying a water extract of *Sargassum horneri* as an active ingredient, and wherein the inflammation is asthma, bronchitis, allergic rhinitis, chronic obstructive pulmonary disease, Lou Gehrig's disease, septicemia, conjunctivitis, purpura, nasal polyp, lupus erythematosus, acute respiratory distress syndrome, Crohn's disease, gastritis, esophagitis, pancreatitis, nephritis, irritable bowel syndrome, mucous colitis, ulcerative colitis, gout, eczema, dermatitis, cystic fibrosis, inflammatory bowel disease or multiple sclerosis.

* * * * *